United States Patent
Ronchi et al.

(10) Patent No.: US 11,123,394 B2
(45) Date of Patent: Sep. 21, 2021

(54) PROCESS FOR THE PREPARATION OF POWDER COMPOSITIONS

(71) Applicant: INDENA S.P.A., Milan (IT)

(72) Inventors: Massimo Ronchi, Milan (IT); Elisabetta Frattini, Milan (IT)

(73) Assignee: INDENA S.P.A., Milan (IT)

( * ) Notice: Subject to any disclaimer, the term of this patent is extended or adjusted under 35 U.S.C. 154(b) by 0 days.

(21) Appl. No.: 16/469,826

(22) PCT Filed: Nov. 30, 2017

(86) PCT No.: PCT/EP2017/080967
§ 371 (c)(1),
(2) Date: Jun. 14, 2019

(87) PCT Pub. No.: WO2018/108549
PCT Pub. Date: Jun. 21, 2018

(65) Prior Publication Data
US 2020/0085901 A1 Mar. 19, 2020

(30) Foreign Application Priority Data

Dec. 15, 2016 (EP) .................................... 16204459

(51) Int. Cl.
| | |
|---|---|
| A61K 36/00 | (2006.01) |
| A61K 36/758 | (2006.01) |
| A61K 9/14 | (2006.01) |
| A61K 36/28 | (2006.01) |
| A61K 36/9068 | (2006.01) |

(52) U.S. Cl.
CPC .............. *A61K 36/758* (2013.01); *A61K 9/14* (2013.01); *A61K 36/28* (2013.01); *A61K 36/9068* (2013.01); *A61K 2236/35* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | | | |
|---|---|---|---|---|
| 6,511,683 | B1* | 1/2003 | Gahler | .................... A61P 37/04 424/737 |
| 2006/0269610 | A1 | 11/2006 | Rosenberg et al. | |
| 2007/0082074 | A1 | 4/2007 | Wang | |
| 2012/0040031 | A1 | 2/2012 | Bombardelli | |
| 2013/0108720 | A1* | 5/2013 | Bombardelli | .............. A61P 1/00 424/737 |
| 2015/0202192 | A1* | 7/2015 | Dikovskiy | ........... A61K 31/732 514/338 |
| 2015/0202246 | A1 | 7/2015 | Bombardelli et al. | |
| 2016/0151441 | A1 | 6/2016 | Bombardelli et al. | |

FOREIGN PATENT DOCUMENTS

| | | |
|---|---|---|
| EP | 2379095 B1 | 7/2013 |
| EP | 2598156 B1 | 5/2014 |
| WO | 2007047003 A2 | 4/2007 |
| WO | 2014016137 A1 | 1/2014 |
| WO | 2015099842 A1 | 7/2015 |

OTHER PUBLICATIONS

International Search Report, dated Feb. 16, 2018, from PCT application No. PCT/EP2017/080967.
Written Opinion, dated Feb. 16, 2018, from PCT application No. PCT/EP2017/080967.
Stefan Raduner et al.; Alkylamides from Echinacea Are a New Class of Cannabinomimetics. Cannabinoid Type 2 Receptor-Dependent And—Independent Immunomodulatory Effects; The Journal of Biological Chemistry; May 19, 2006; p. 14192-14206; vol. 281 No. 20, The American Society for Biochemistry and Molecular Biology, Inc.
Katina S. S. Dossou et al.; Identification of CB1/CB2 Ligands from Zanthoxylum bungeanum; Journal of Natural Products; Oct. 31, 2013; p. 2060-2064; The American Chemical Society and American Society of Pharmacognosy.
Swarnalatha Dugasani et al.; Comparative antioxidant and anti-inflammatory effects of [6]-gingerol, [8]-gingerol, [10]-gingerol and [6]-shogaol; Journal of Ethnopharmacology; Feb. 3, 2010; p. 515-520; vol. 127, Issue 2.
Juerg Gertsch et al.; Echinacea alkylamides modulate TNF-α gene expression via cannabinoid receptor CB2 and multiple signal transduction pathways; Nov. 19, 2004; p. 563-569; vol. 577, Issue 3.

* cited by examiner

*Primary Examiner* — Qiuwen Mi
(74) *Attorney, Agent, or Firm* — Nixon & Vanderhye

(57) ABSTRACT

Disclosed is a process for the preparation of powder compositions including a lipophilic extract of *Echinacea* spp., a lipophilic extract of *Zingiber officinale* and phospholipids. Also disclosed are powder compositions obtainable by the process and pharmaceutical, nutraceutical and cosmetic formulations including the compositions. Also described is a use of the powder compositions and formulations thereof in the prevention and/or treatment of inflammatory and painful states.

19 Claims, No Drawings

PROCESS FOR THE PREPARATION OF POWDER COMPOSITIONS

TECHNICAL FIELD OF THE INVENTION

The present invention relates to a process for the preparation of powder compositions comprising a lipophilic extract of *Echinacea* spp., a lipophilic extract of *Zingiber officinale* and phospholipids.

The invention also relates to the powder compositions obtainable by the process of the invention and pharmaceutical, nutraceutical and cosmetic formulations comprising said compositions.

The powder compositions according to the invention, and formulations thereof, are useful in the prevention and/or treatment of inflammatory and painful states.

BACKGROUND OF THE INVENTION

Lipophilic extracts of *Echinacea* spp., preferably those of *Echinacea angustifolia*; *Zanthoxylum* spp., preferably those of *Zanthoxylum bungeanum*; *Acmella* spp., preferably those of *Acmella oleracea*, possess anti-inflammatory activity when administered either topically or systemically. It has been demonstrated that their pharmacological activity can be attributed to isobutylamides, ligands of the CB1 and CB2 cannabinoid receptors (*Alkylamides from Echinacea are a new class of cannabinomimetics*; Stefan Raduner et al.; *J. Biol. Chem.* (2006), 281(20), 14192-14206. *Identification of CB1/CB2 Ligands from Zanthoxylum bungeanum*; Katina S. S. Dossou et al.; *J. Nat. Prod.* 2013, 76, 2060-2064).

The main active components of the lipophilic extract of *Zingiber officinale* consist of gingerols and shogaols. Gingerols and shogaols are potent inhibitors of LPS(lipopolysaccharide)-induced PGE2 (Prostaglandin E2) production and lipoxygenase pleiotropic down-modulators of pro-inflammatory cytokines at site of inflammation. Moreover gingerols and shogaols are potent vanilloid receptor (VR1) agonists (*Comparative antioxidant and anti-inflammatory effects of [6]-gingerol, [8]-gingerol, [10]-gingerol and [6]-shogaol*; Swarnalatha Dugasania et al.; *J. Ethnopharmacol.* 127 (2010) 515-520. *Gingerols: a novel class of vanilloid receptor (VR1) agonists*; Vadim N. Dedov et al., Brit. J. Pharmacol. (2002) 137, 793-798. *Echinacea alkylamides modulate TNF-α gene expression via cannabinoid receptor CB2 and multiple signal transduction pathways*; Juerg Gertscha et al.; FEBS Letters 577 (2004) 563-569).

It has been described that a formulations containing lipophilic extracts of *Echinacea angustifolia* and *Zingiber officinale* are useful in reducing inflammation and peripheral pain (EP 2 598 156 B1) and for the prevention and treatment of gastroesophageal reflux (EP 2 379 095 B1).

Taking into account that lipophilic extracts of *Echinacea angustifolia* (or *Zanthoxylum*, or *Acmella*) and *Zingiber officinale* are in oily physical state, soft gelatin capsules represent the ideal formulation for their oral administration. It is well known that the systemic absorption of poorly soluble active ingredients, formulated as lipid-based fills for soft gelatin capsules, can be mediated and enhanced by the digestion process of triglycerides. Moreover, the oral bioavailability of the poorly soluble active ingredient administered as lipid based fills of soft gelatin capsules can be also enhanced by the transport to the systemic circulation via intestinal lymphatic system.

On the other side, soft gelatin capsule formulations are characterized by some disadvantages, due to the fact that the active ingredients are often more susceptible to chemical degradation and physical instability of the dosage form, due to the interaction between the active substances and the gelatin shell. This particularly occurs for botanical extracts, due to their multi-component chemical composition. Furthermore, the production of soft gelatin capsules requires specific facilities and equipment which are available only from a limited number of companies.

Therefore, there is still the need of alternative compositions characterized by a high and fast absorption of the active ingredients, that can be easily incorporated in stable formulations.

SUMMARY OF THE INVENTION

The present invention concerns a process for the preparation of powder compositions comprising the following steps:

a) a lipophilic extract of *Echinacea* spp., or a botanical lipophilic extract containing alkylamides, and a lipophilic extract of *Zingiber officinale* are dispersed in at least one organic solvent and kept under mixing until a solution or a suspension is obtained; heating is optionally applied;

b) at least one phospholipid is then added to the solution, or suspension, of the lipophilic extracts and the mixture is kept under mixing; heating is optionally applied;

c) the organic solvent is then removed to obtain the powder composition.

The invention also relates to the powder compositions obtainable by the process of the invention and to pharmaceutical, nutraceutical and cosmetic formulations comprising said compositions.

The powder compositions according to the invention are useful in the prevention and/or treatment of inflammatory and painful states.

DETAILED DESCRIPTION OF THE INVENTION

It has been surprisingly found that powder compositions containing a lipophilic extract of *Echinacea* spp. (or other botanical extracts containing alkylamides) and a lipophilic extract of *Zingiber officinale* combined with phospholipids, prepared according to the manufacturing process described in the present invention, is useful for the preparation of solid formulations, such as conventional dosage forms other than soft gels, like tablets and hard gelatin capsules, and the resulting solid formulations guarantee a similar or an improved (higher and/or faster) absorption of the active ingredients, leading to a rapid onset of the pharmacological effect, compared to a soft gelatin capsule formulation comprising in turn a mechanical mixture of the same active ingredients.

The present invention relates to a manufacturing process for preparing a powder composition comprising the following components: a lipophilic extract of *Echinacea* spp. (or other botanical extracts containing alkylamides, such as *Zanthoxylum* spp. or *Acmella* spp.), a lipophilic extract of *Zingiber officinale* and phospholipids, the process of the invention is able to guarantee an intimate interaction between the lipophilic extracts and phospholipids. This intimate interaction can be obtained through the total or partial co-solubilisation of the lipophilic extracts in a suitable organic solvent prior to the addition of the phospholipids.

The manufacturing process for preparing a powder composition according to the present invention comprises the following steps:

a) a lipophilic extract of *Echinacea* spp., or a botanical lipophilic extract containing alkylamides, and a lipophilic extract of *Zingiber officinale* are dispersed in at least one suitable organic solvent and kept under mixing until a solution or a suspension is obtained; heating is optionally applied, if required;

b) at least one phospholipid is then added to the solution of the lipophilic extracts and the mixture is kept under mixing; heating is optionally applied;

c) the organic solvent is then removed to obtain the powder composition.

The lipophilic extract of *Echinacea* spp. is preferably obtained from *Echinacea angustifolia* or *purpurea*, more preferably from *Echinacea angustifolia*.

Other botanical lipophilic extracts containing alkylamides may be used, such extracts may be, for example, lipophilic extracts of *Zanthoxylum* spp. or *Acmella* spp. Preferably, the lipophilic extracts of *Zanthoxylum* spp. may be obtained from *Zanthoxylum bungeanum, Zanthoxylum piperitum, Zanthoxylum americanum* and the lipophilic extracts of *Acmella* spp. from *Acmella oleracea*.

The suitable organic solvent is a polar organic solvent that leads to a total or at least substantial solubilisation of the lipophilic extracts, such as polar protic solvent or a polar aprotic solvent.

Preferably the polar protic solvent is a, straight or branched, $C_1$-$C_8$ alkyl alcohol and the polar aprotic solvent is a, straight or branched, $C_1$-$C_8$ alkyl ester or a $C_1$-$C_8$ dialkyl ketone.

A total or event partial solubilisation of the phospholipids in the selected organic solvent is also desirable.

The preferred organic solvent may be selected from the group comprising ethyl alcohol, ethyl acetate, acetone, isopropyl alcohol, isobutyl alcohol, and combinations thereof. Ethyl alcohol and ethyl acetate are preferred.

Heating is optionally applied to facilitate solubilisation without causing any degradation of the active ingredients.

The phospholipid may be selected from lecithins derived from soy, sunflower or egg, phosphatidyl choline, phosphatidyl serine, phosphatidyl ethanolamine, wherein the acyl groups may be the same or different and are mostly derived from palmitic, stearic, oleic, linoleic, linolenic acids; and combinations thereof. Preferably, the phospholipid is lecithin.

The lipophilic extracts to phospholipid ratio may preferably range from 0.2 to 2, more preferably from 0.5 to 1.

After step b) additional ingredients may be added to the obtained solution (or suspension) of lipophilic extracts and phospholipid, which is kept under mixing for a suitable period of time to facilitate the interaction of the different ingredients.

A second surfactant, other than lecithin, may be included in the powder composition, for example, to further promote the dissolution of the active ingredients of the lipophilic extracts and to enhance their fast absorption. The second surfactant may be selected from the group comprising polyoxyethylene castor oil derivatives, polyoxyethylene sorbitan fatty acid esters, polyglycerides, sorbitan fatty acid esters, sucrose palmitate, sucrose stearate, D-α-tocopheryl polyethylene glycol succinate, and combinations thereof.

The phospholipid (for example lecithin) to second surfactant ratio may preferably range from 0.25 to 10, most preferably from 0.5 to 1.

The solvent may be removed under vacuum. Alternative drying method may also be used to remove the organic solvent, such as spray drying and freeze drying.

The obtained powder composition usually is then calibrated and eventually grinded to obtain the desired particle size distribution.

The invention also relates to the powder compositions obtainable by the manufacturing process of the invention comprising a lipophilic extract of *Echinacea* spp., or other botanical lipophilic extracts containing alkylamides, a lipophilic extract of *Zingiber officinale* and one or more phospholipids.

The resulting compositions are in powder form and they can be easily incorporated, through conventional manufacturing methods, in solid dosage forms, such as tablets, hard gelatin capsules and granulates. The powder compositions are characterized by a fast and effective absorption of the active ingredients and by a consequent fast onset of their pharmacological activity. Consequently, an improved and faster solubilisation in gastric environment can further enhance, both from a quantitative and kinetic point of view, gingerols, shogaols and alkylamides absorption in the systemic circulation, promoting a higher bioavailability and a rapid onset of their pharmacological activity.

Additional ingredients may also be added to the powder compositions with the purpose to further enhance the extent and the speed of the systemic absorption of the active ingredients and improve the technological characteristics of the compositions to facilitate their incorporation in solid dosage forms through conventional manufacturing methods. This ingredients may be selected, for example, from microcrystalline cellulose, calcium phosphate, powdered cellulose, calcium sulphate, magnesium sulphate, methylcellulose, hydroxypropyl cellulose, carboxymethyl cellulose, hydroxypropylmethyl cellulose, fructose, mannitol, maltodextrins, cyclodextrins, isomalt, dextrins, inulin.

Additional ingredients may also be added to the powder composition to improve its flowability. This excipients may be, for example, silicon dioxide and talc.

The present invention also relates to pharmaceutical, nutraceutical and cosmetic formulations comprising a powder composition obtained through the manufacturing process of the invention and at least one physiologically acceptable excipient and/or carrier.

Preferably the formulations are for oral administration.

Physiologically acceptable excipients and/or carriers, may be, for example, disintegrant, lubricant, binder, coating agent, colorant, absorption enhancer, solubilizing agent, stabilizer, flavor, sweetener, antiseptic, preservative, antioxidant and the like.

Examples of dosage forms of the formulations of the invention may be tablets, chewable tablets, hard gelatin capsules, powder for reconstitution.

The powder compositions, as such or included in solid dosage forms, are characterized by an effective and fast absorption of the active ingredients of the lipophilic botanical extracts, by a high oral bioavailability of these active ingredients and, consequently, by a rapid onset of their pharmacological activities.

The powder compositions obtained through the manufacturing method described in the present invention and solid formulations thereof, i.e. the dosage forms containing the powder compositions, are useful in the prevention and/or treatment of different inflammatory and painful states, particularly when a rapid onset of the pharmacological effect is required.

The dry powder compositions obtained according to the manufacturing process described in the present invention were tested to evaluate the solubility of the active ingredients. The solubility was measured in water and/or in biorelevant media (simulating gastric and intestinal fluids in fasted and fed conditions) and compared with the solubility of the oily lipophilic extracts formulated as fillers for soft gelatin capsules and with the solubility of the physical (mechanical) mixture of the components.

The powder compositions were analyzed by HPLC for determining the content of the active ingredients of the lipophilic extracts and residual solvent(s).

The following non-limitative examples further describe the invention.

EXAMPLES

Example 1

Preparation of a Powder Composition 50 g of *Zingiber officinale* lipophilic extract and 10 g of *Echinacea angustifolia* lipophilic extract are dissolved under mixing in 2000 mL of ethyl acetate. A clear solution is obtained.

60 g of sunflower lecithin are added to the obtained solution of the lipophilic extracts, mixing at 60° C. for 2 hours until almost complete solubilisation of the lecithin is obtained.

250 g of microcrystalline cellulose and 24 g of hydroxypropylmethyl cellulose are added to the solution of the lipophilic extracts and lecithin, mixing for about one hour.

The solvent was then removed under reduced pressure to a residue of ethyl acetate lower than 5000 ppm.

8 g of silicon dioxide are added to the dried powder to improve its flowability.

The resulting solid was calibrated through a 1 mm screen to obtain a brownish, flowable powder.

Example 2

Preparation of a Powder Composition 37.5 g of *Zingiber officinale* lipophilic extract and 7.5 g of *Acmella oleracea* lipophilic extract are dissolved under mixing in 2500 mL of ethyl alcohol. A clear solution is obtained.

45 g of sunflower lecithin are added to the obtained solution of the lipophilic extracts, mixing at 60° C. for 2 hours until almost partial solubilisation of the lecithin is obtained.

235 g of microcrystalline cellulose and 18 g of hydroxypropyl cellulose are added to the obtained organic suspension, mixing for about one hour.

The solvent was then removed under reduced pressure to a residue of ethyl alcohol lower than 5000 ppm.

7 g of silicon dioxide are added to the dried powder to improve its flowability.

The resulting solid was calibrated through a 1 mm screen to obtain a brownish, flowable powder.

Example 3

Preparation of a Powder Composition 125 g of *Zingiber officinale* lipophilic extract and 25 g of *Echinacea angustifolia* lipophilic extract are dissolved under mixing in 5 L of ethyl acetate. A clear solution is obtained.

150 g of sunflower lecithin are added to the solution of the lipophilic extracts, mixing for about two hours at 60° C. until almost complete solubilization of the lecithin is obtained.

125 g of sucrose palmitate are added to the obtained solution, mixing for about 15 minutes at 60° C. 750 g of microcrystalline cellulose are then added to the obtained solution, mixing for about 15 minutes.

The solvent was then removed under reduced pressure, until a residual of ethyl acetate lower than 5000 ppm. 20 g of silicon dioxide are added to the obtained powder.

The resulting solid was calibrated through a 1 mm screen to obtain a flowable brownish powder.

Example 4

Preparation of a Powder Composition 37.5 g of *Zingiber officinale* lipophilic extract and 7.5 g of *Acmella oleracea* lipophilic extract are dissolved under mixing in 4 L of ethyl alcohol. A clear solution is obtained.

45 g of sunflower lecithin are added to the solution of the lipophilic extracts, mixing for about two hours at 60° C. until almost partial solubilisation of the lecithin is obtained.

35 g of sucrose palmitate are added to the obtained organic suspension, mixing for about 15 minutes at 60° C. 200 g of microcrystalline cellulose and 18 g of hydroxypropyl cellulose are then added to the obtained solution, mixing for about 15 minutes.

The solvent was then removed under reduced pressure, until a residual of ethyl alcohol lower than 5000 ppm. 7 g of silicon dioxide are added to the obtained powder.

The resulting solid was calibrated through a 1 mm screen to obtain a flowable brownish powder.

Example 5

Solubility Study

About 200 mg of the powder composition described in Example 3 were suspended in 10 ml of simulated gastric fluid and magnetically stirred for 2 hours at room temperature in a suitable container. The suspension was then filtered through a 0.2 µm PTFE disposable syringe filter and the clear water-phase was directly injected into the HPLC system for analysis.

The same procedure was also applied to a physical (mechanical) mixture containing the same components of the formulation described in Example 3.

The following results, expressed as concentration of the sum of gingerols and shogaols, which are the active ingredients of *Zingiber officinale* lipophilic extract, were obtained:

Formulation according to Example 3=0.035 mg/ml
Physical (mechanical) mixture=0.024 mg/ml An increase of about 46% of the solubility of gingerols+shogaols was observed for the formulation obtained according to Example 3 compared to the physical (mechanical) mixture. A faster and higher solubilisation of the active ingredients in gastric fluid may enhance their fast absorption and a faster onset of their pharmacological activity, which is particularly useful in pain management.

Example 6

Solubility Study

About 200 mg of the powder composition obtained in Example 3 were suspended in 10 ml of simulated gastric fluid and magnetically stirred for 2 hours at room temperature in a suitable container. The suspension was then filtered through a 0.2 μm PTFE disposable syringe filter and the clear water-phase was directly injected into the HPLC system for analysis.

The same procedure was also applied to a physical (mechanical) mixture containing the same components of the formulation described in Example 3.

The following results, expressed as concentration of alkylamide 8, which is one of the most relevant active ingredients of *Echinacea angustifolia* lipophilic extract, were obtained:

Formulation according to Example 3=0.027 mg/ml
Physical mixture=0.012 mg/ml

A significant increase of the solubility of alkylamide 8 was observed for the formulation obtained in Example 3 compared to the physical (mechanical) mixture. A faster and higher solubilisation of the active ingredients in gastric fluid may enhance their fast absorption and a faster onset of their pharmacological activity, which is particularly useful in pain management.

Example 7

The solubility of gingerols and shogaols in simulated gastric fluid from the composition described in Example 3 was measured and compared to the solubility of gingerols and shogaols from an oily composition suitable to be filled in soft gelatin capsules. It is well known that soft gelatin capsule formulations can promote the bioavailability of poorly soluble active ingredients. The results of the experiment were the following, expressed as concentration of the sum of gingerols and shogaols:

Formulation according to Example 3=0.344 mg/ml
Oily composition for soft gelatin capsules=0.090 mg/ml The concentration of gingerols and shogaols (sum) in simulated intestinal fluid from the formulation described in Example 3 resulted to be 3.8 times higher than the concentration of gingerols and shogaols from the oily composition suitable for soft gelatin capsules.

Example 8

Solubility Study

The solubility of gingerols and shogaols in simulated intestinal fluid from the formulation described in Example 1 was measured and compared to the solubility of gingerols and shogaols from an oily composition suitable to be filled in soft gelatin capsules. The results of the experiment, expressed as concentration of the sum of gingerols and shogaols, are reported below:

Formulation according to Example 1=0.444 mg/ml
Oily composition for soft gelatin capsules=0.149 mg/ml The concentration of gingerols and shogaols (sum) in simulated intestinal fluid from the formulation described in Example 1 resulted to be three times higher than the concentration of gingerols and shogaols from the oily composition for soft gelatin capsules.

Example 9

Tablet Dosage Form

| | |
|---|---|
| Powder composition (Example 1) | 200.0 mg |
| Microcrystalline cellulose | 200.0 mg |
| Dicalcium phosphate dihydrate | 75.0 mg |
| Sodium croscarmellose | 15.0 mg |
| Magnesium stearate | 5.0 mg |
| Silicon dioxide | 5.0 mg |

The powder composition described in Example 1 is blended with microcrystalline cellulose, dicalcium phosphate dihydrate and sodium croscarmellose in a suitable mixer for 10 minutes. Magnesium stearate and silicon dioxide are then added to the obtained mixture and blended for additional 2 minutes. The obtained mixture is compressed in a rotary tableting machine equipped with round concave punches with a diameter of 10 mm, dosing 500 mg tablet. The obtained tablets are characterized by suitable hardness, friability and disintegration time.

Example 10

Hard Gelatin Capsule Dosage Form

| | |
|---|---|
| Powder composition (Example 4) | 350.0 mg |
| Dicalcium phosphate anhydrous | 80.0 mg |
| Polyvinylpolypyrrolidone | 12.0 mg |
| Glyceryl behenate | 4.0 mg |
| Silicon dioxide | 4.0 mg |

The powder composition described in Example 4 is blended with dicalcium phosphate anhydrous and polyvinylpolypyrrolidone in a suitable mixer for 10 minutes. Glyceryl behenate and silicon dioxide are then added to the obtained mixture and blended for additional 2 minutes. The obtained mixture was filled in size 1 hard gelatin capsules, dosing 350 mg capsule.

The invention claimed is:

1. A powder composition obtainable by a manufacturing process comprising the following steps:
   a) dispersing a lipophilic extract of *Echinacea* spp., or a botanical lipophilic extract containing alkylamides selected from a lipophilic extract of *Zanthoxylum* spp. or *Acmella* spp., and a lipophilic extract of *Zingiber officinale* in at least one polar organic solvent and mixing until a solution or a suspension is obtained;
   b) adding at least one phospholipid to the solution, or suspension, of the lipophilic extracts and mixing the mixture;
   c) removing the organic solvent to obtain the powder composition;
   wherein a weight ratio of the lipophilic extracts to the at least one phospholipid is from 0.2 to 2.

2. The powder composition of claim 1, wherein the weight ratio of the lipophilic extracts to the at least one phospholipid is from 0.5 to 1.

3. The powder composition of claim 2, wherein the weight ratio of the lipophilic extracts to the at least one phospholipid is 1.

4. The powder composition of claim 1, wherein the lipophilic extract is obtained from *Acmella oleracea*.

5. The powder composition of claim 1, wherein the phospholipid is selected from lecithins derived from soy, sunflower or egg, phosphatidyl choline, phosphatidyl serine, phosphatidyl ethanolamine, wherein acyl groups are the same or different and are mostly derived from palmitic, stearic, oleic, linoleic, linolenic acids; and combinations thereof.

6. The powder composition of claim 4, wherein the phospholipid is lecithin.

7. The powder composition of claim 6, wherein the lecithin is sunflower lecithin.

8. The powder composition of claim 1, wherein after step b) an additional ingredient is added to the solution or suspension obtained in step a).

9. The powder composition of claim 8, wherein the additional ingredient is a second surfactant, other than lecithin.

10. The powder composition of claim 9, wherein the second surfactant is selected from the group consisting of polyoxyethylene castor oil derivatives, polyoxyethylene sorbitan fatty acid esters, polyglycerides, sorbitan fatty acid esters, sucrose palmitate, sucrose stearate, D-α-tocopheryl polyethylene glycol succinate, and combinations thereof.

11. The powder composition of claim 9, wherein a weight ratio of the phospholipid to second surfactant is from 0.25 to 10.

12. The powder composition of claim 11, wherein the weight ratio of the phospholipid to second surfactant is from 0.5 to 1.

13. The powder composition of claim 11, wherein the weight ratio of the phospholipid to second surfactant is from 1.2 to 10.

14. The powder composition of claim 1, wherein a weight ratio of the lipophilic extract of *Echinacea* spp., or a botanical lipophilic extract containing alkylamides selected from a lipophilic extract of *Zanthoxylum* spp. or *Acmella* spp. to the lipophilic extract of *Zingiber officinale* is 0.2.

15. Pharmaceutical, nutraceutical and cosmetic formulations comprising a powder composition according to claim 1 and at least one physiologically acceptable excipient and/or carrier.

16. A powder composition obtainable by a manufacturing process comprising the following steps:
  a) dispersing a lipophilic extract of *Echinacea* spp. from 10 g to 25 g, or a botanical lipophilic extract containing alkylamides selected from a lipophilic extract of *Zanthoxylum* spp. or *Acmella* spp. equal to 7.5 g, and a lipophilic extract of *Zingiber officinale* from 37.5 g to 125 g in at least one polar organic solvent and mixing until a solution or a suspension is obtained;
  b) adding at least one phospholipid from 45 to 150 g to the solution, or suspension, of the lipophilic extracts and mixing the mixture;
  c) removing the organic solvent to obtain the powder composition;
  wherein a weight ratio of the lipophilic extracts to the at least one phospholipid is from 0.2 to 2.

17. The powder composition of claim 1, wherein after step b) additional ingredients are added to the obtained solution, or suspension, of lipophilic extracts and phospholipid, which is kept under mixing.

18. The powder composition of claim 17, wherein the additional ingredients are selected from microcrystalline cellulose, powdered cellulose, methylcellulose, hydroxypropyl cellulose, carboxymethyl cellulose, hydroxypropylmethyl cellulose.

19. The powder composition of claim 17, wherein the additional ingredients are selected from microcrystalline cellulose, hydroxypropyl cellulose.

* * * * *